United States Patent

Morita et al.

[11] Patent Number: 5,116,552
[45] Date of Patent: May 26, 1992

[54] PROCESS FOR PREPARATION OF DRIED COLLAGEN SPONGE

[75] Inventors: Shinichiro Morita; Nobuya Takahashi, both of Ayabe; Takeshi Shimamoto, Fukuchiyama; Kazuya Matsuda; Shigehiko Suzuki, both of Kyoto, all of Japan

[73] Assignee: Gunze Limited, Kyoto, Japan

[21] Appl. No.: 646,034

[22] Filed: Jan. 28, 1991

[30] Foreign Application Priority Data

Jan. 31, 1990 [JP] Japan .................. 2-22860

[51] Int. Cl.$^5$ ............................. B29B 13/04
[52] U.S. Cl. ........................ 264/28; 8/94.11; 264/101; 427/244
[58] Field of Search ............ 8/94.11; 264/28, 101; 427/244

[56] References Cited

U.S. PATENT DOCUMENTS

| | | | |
|---|---|---|---|
| 2,610,625 | 9/1952 | Sifferd et al. | 8/94.11 |
| 3,157,524 | 11/1964 | Artandi | 264/28 |
| 4,412,947 | 11/1983 | Cioca | 264/28 |
| 4,948,540 | 8/1990 | Nigam | 264/28 |

FOREIGN PATENT DOCUMENTS

| | | |
|---|---|---|
| 52-46282 | 11/1977 | Japan . |
| 54-3779 | 2/1979 | Japan . |
| 61-41452 | 2/1986 | Japan . |
| 61-16459 | 4/1986 | Japan . |

*Primary Examiner*—Jan H. Silbaugh
*Assistant Examiner*—Brian J. Eastley
*Attorney, Agent, or Firm*—Armstrong & Kubovcik

[57] ABSTRACT

A process for preparing a crack-free, dried collagen sponge having a shrinkage factor of up to 14%, including the steps of impregnating crosslinked collagen sponge with an aqueous solution of a hydrophilic organic solvent, freezing the sponge at a temperature of −80° C. or lower, and vacuum-drying the sponge.

5 Claims, No Drawings

PROCESS FOR PREPARATION OF DRIED COLLAGEN SPONGE

BACKGROUND OF THE INVENTION

1. Field of the Invention

The present invention relates to a process for preparing a dried collagen sponge.

2. Prior Art

Collagen sponge is widely used as materials for medical articles such as artificial skins. The collagen sponge is generally prepared by the following method. An aqueous solution of atelocollagen is placed into a suitable mold directly or, when required, after homogenization with ice-cooling, the molded body is lyophilized to give a microporous sponge, and the obtained sponge is crosslinked as follows. The lyophilized sponge is heated at a temperature of about 100° to about 110° C. to cause intramolecular crosslinking which imparts water resistance, and further treated in the presence of a crosslinking agent to induce intermolecular crosslinking which renders the sponge resistant to hydrolyzation with collagenase. The term "crosslinking" used herein includes the above-mentioned intramolecular crosslinking and intermolecular crosslinking. After crosslinking treatment, the sponge is washed with distilled water or physiological saline to remove the crosslinking agent. Thereafter the distilled water or saline is replaced with an aqueous solution of alcohol. The sponge as immersed in the alcohol solution is stored in a hermetically closed container from which the sponge is taken out before use. In use, the alcohol solution in the sponge is replaced with physiological saline and then the sponge is provided for use, e.g., as an artificial skin.

However, the collagen sponge stored in the wet state as described above changes its properties and disadvantageously becomes unsuitable for use as an artificial skin. The wet sponge, moreover, is inconvenient to handle as in packaging, transporting or sterilization, incurring increased costs, hence is undesirable.

To resolve this problem, the present inventors have made the following attempt. The collagen sponge prepared and crosslinked in a conventional manner is directly lyophilized again, sterilized and stored as dried instead of being stored as immersed in an alcohol solution. In the experiment, the crosslinked collagen sponge was washed with physiological saline or distilled water to remove the crosslinking agent. Then the sponge was lyophilized again whereupon, however, the sponge became pronouncedly shrunk and gave a hard surface feel, in other words, shrank so much as to be unfit for use as an artificial skin. The inventors also performed lyophilization at a lower temperature to prevent contraction, but found that the sponge easily cracked during drying, reducing its usefulness as an artificial skin. To our best knowledge, crosslinked collagen sponge which can be stored in a dry state has not been provided for these reasons.

SUMMARY OF THE INVENTION

It is an object of the present invention to provide collagen sponge which is free of the foregoing problems and which can be stored in a dry state without change of properties for an extended period of time and a process for preparing the dried collagen sponge.

It is another object of the invention to provide a process for preparing dried collagen sponge, the process being capable of lyophilizing crosslinked collagen sponge without causing the undesired contraction and cracking.

These and other objects of the invention will become more apparent from the following description.

According to the present invention, there is provided a process for preparing collagen sponge, the process comprising the steps of impregnating crosslinked collagen sponge with an aqueous solution of a hydrophilic organic solvent, freezing the sponge at a temperature of about −80° C. or lower, and vacuum-drying the sponge.

DETAILED DESCRIPTION OF THE INVENTION

Our research revealed the following. When a crosslinked collagen sponge is impregnated with an aqueous solution of a hydrophilic organic solvent before lyophilization, lyophilization can be done without involving cracks at a low temperature of about −80° C. or below sufficient to prevent the contraction of sponge, giving dried collagen sponge having a surface feel like that of artificial skins. The dried collagen sponge can be stored in a dry state without change of properties for an extended period of time. The present invention has been accomplished based on these novel findings.

The crosslinked collagen sponge for use in the invention can be prepared by lyophilizing an aqueous solution of atelocollagen into sponge in a conventional manner and subjecting the sponge to intramolecular crosslinking reaction by heating to impart water resistance and to intermolecular crosslinking reaction in the presence of a crosslinking agent to impart resistance to hydrolyzation with collagenase. An aqueous solution of atelocollagen can be prepared in a conventional manner by causing protease at an acidity range to act on an animal tissue having a high content of collagen such as mammal's skins, intestines, tendons, etc. in order to solubilize the collagen. The aqueous solution of the atelocollagen is adjusted to a concentration of about 0.2 to about 5 w/v %, and when required, homogenized with stirring and ice-cooling to induce foaming. Subsequently the atelocollagen solution is placed into a suitable mold, frozen and dried to give microporous sponge. The freezing and drying may be conducted under conventional conditions. The sponge is frozen at a low temperature of about −20° to about −50° C. and vacuum-dried at a temperature of about −30° to about 40° C. in a vacuum of about 0.01 to about 0.2 mmHg. The sponge obtained in this stage is white in color, and has pores with a mean diameter of about 5 to about 1000 μm, favorably about 50 to about 120 μm and a void percentage of about 90 to about 99%.

The thus obtained sponge is heated to cause intramolecular crosslinking which imparts water resistance. A preferred heating temperature is in the range of about 100° to about 110° C. When required, the heating may be conducted in a vacuum to increase the degree of drying. Then the sponge is treated in the presence of a crosslinking agent to undergo intermolecular crosslinking reaction, whereby the sponge is made resistant to hydrolyzation with collagenase. Examples of useful crosslinking agents are various and include conventional ones such as formaldehyde, hexamethylene diisocyanate, glutaraldehyde and the like. The crosslinking reaction is effected in a conventional manner by immersing the sponge in a solution of a crosslinking agent at room temperature or with cooling, usually in the range of about 4° to about 25° C.

The crosslinked sponge is continuously washed with distilled water to replace the solution of crosslinking agent therewith until the crosslinking agent is completely removed. The procedures up to the foregoing step are conventional in the art and not limitative. Various known methods are applicable to obtain the crosslinked collagen sponge to be treated by the process of the invention.

According to the invention, an aqueous solution of hydrophilic organic solvent is impregnated into the thus obtained collagen sponge. Examples of useful hydrophilic organic solvents are methanol, ethanol, propanol and like lower aliphatic alcohols, acetone and like lower aliphatic ketones, etc. among which lower aliphatic alcohols are preferred and ethanol is most preferred. A suitable concentration of the hydrophilic organic solvent in the aqueous solution, although variable depending on the type of organic solvent, is in the range of about 5 to about 50% by weight, preferably about 10 to about 30% by weight.

An aqueous solution of a hydrophilic organic solvent can be impregnated into the sponge in the following manner. The sponge containing the washings left after the crosslinking reaction may be directly immersed into an aqueous solution of organic solvent to replace the washings. Alternatively the sponge may be impregnated with the solution by immersion, spraying or other suitable methods after the removal of washings by drying, squeezing, rubbing or the like. The solution may be continuously circulated during the impregnation process. Optionally the sponge may be squeezed, rubbed or otherwise suitably treated to achieve more efficient impregnation. The sponge is impregnated with the solution so that the solution accounts for at least 90% by volume of the sponge.

According to the invention, the sponge impregnated in this manner with the aqueous solution of hydrophilic organic solvent is frozen at a low temperature of about −80° C. or lower. When the freezing temperature is higher than about −80° C., contraction is likely to occur. In the present invention, the freezing is accomplished without cracking at a lower temperature of about −80° C. or below at which contraction can be avoided. A preferred freezing temperature is about −80° to about −135° C. The frozen sponge is dried in a conventional manner at a temperature of about −30° to about 40° C. in a vacuum of about 0.01 to about 0.2 mmHg.

The collagen sponge obtained according to the invention is free of cracks and shows a markedly low shrinkage factor of up to 14%, favorably up to 12%. The sponge has pores with an average diameter of about 5 to about 1000 $\mu$m, favorably about 50 to about 120 $\mu$m and a void ratio of about 90 to about 99% and feels as soft as artificial skins. Consequently the sponge of the invention can be advantageously used as artificial skins.

The dried collagen sponge of the invention is sterilized and can be stored for an extended period of time under sterilizing conditions. Even after a long period of storage, e.g. storage for 1 to 3 years, the collagen sponge of the invention shows no change in properties. The sterilization may be conducted by conventional methods commonly employed for medical materials as by application of an ethylene oxide gas or by irradiation of gamma rays. The sterilized collagen sponge of the invention may be stored in a hermetically closed sterilized bag made of aluminum or the like.

The present invention will be described below in more detail with reference to the following Examples and Comparison Examples.

EXAMPLES 1 AND 2

A 50 g quantity of atherocollagen (conc. 0.3 w/v %, pH 3.0) derived from pig's tendon was homogenized with ice-cooling (with stirring at 1800 to 2000 r.p.m. for 60 minutes), placed into a mold of aluminum having a rectangular cavity, 10 cm in length, 7.6 cm in width and 1.5 cm in depth, and rapidly frozen at −40° C. The frozen molded body was dried at 30° C. for 48 hours in a vacuum of 0.1 mmHg to give a sponge. The sponge was then dried under vacuum with heating at 105° C. for 24 hours to undergo intramolecular crosslinking reaction. The sponge was immersed in a 0.2 wt. % solution of glutaraldehyde in 0.05M acetic acid and caused to undergo intermolecular crosslinking reaction at 4° C. for 24 hours. The solution was continuously washed with distilled water to replace the solution until complete removal of glutaraldehyde. The obtained sponge was light yellow in color and had pores with an average diameter of 50 to 120 $\mu$m.

The crosslinked sponge was then immersed in a 15 wt % aqueous solution of ethanol to replace the distilled water therewith and rapidly frozen in an extremely low-temperature refrigerator at −80° C. (Example 1) or −135° C. (Example 2). The completely frozen sponge was dried at 30° C. in a vacuum of about 0.1 mmHg for 24 hours in a device for vacuum lyophilization.

In this way, collagen sponges (in Examples 1 and 2) were produced. The sponges were found to be crack-free and light yellow in color and to be sponge-like with pores of 50 to 120 $\mu$m in diameter.

COMPARISON EXAMPLE 1

A crosslinked sponge impregnated with distilled water was lyophilized in the same manner as in Example 1 without replacing the distilled water with the aqueous solution of ethanol.

The obtained collagen sponge specimen was found to have multiple cracks and to give an exceedingly impaired appearance, and thus was unfit for use as artificial skins.

COMPARISON EXAMPLE 2

A collagen sponge specimen was prepared in the same manner as in Example 1 except that the crosslinked sponge was lyophilized at −40° C.

The sponges prepared in Examples 1 and 2 and Comparison Example 2 were tested for properties by the following methods.

Test for Shrinkage Factor

The length and width of the crosslinked sponges obtained in Example 1 and 2 and Comparison Example 2 were measured at three points of each sponge by slide calipers before and after lyophilization. The mean values of measurements were multiplied to give an area value. The shrinkage factor was expressed in terms of a percent decrease of area as calculated from the difference between the area values obtained before and after the lyophilization.

Three sponges prepared in each of Examples and Comparison Examples were used to provide an average of three measurements. Table 1 below shows the results.

TABLE 1

|  | Comp. Example 2 | Example 1 | Example 2 |
| --- | --- | --- | --- |
| Lyophilizing temperature (°C.) | −40 | −80 | −135 |
| Shrinkage factor (%) | 15.1 | 13.1 | 11.3 |

The usefulness of sponge specimens as artificial skins was evaluated by a dermatologist. The results are as follows. The sponge specimen (Comparison Example 2) which was prepared by lyophilizing at −40° C. and contracted at a ratio of 15.1% gave a hard feel, and was not proper for use.

The sponge specimens involving the lyophilization at −80° C. and −135° C. were soft and suited for use. The sponge specimen obtained by treatment at −135° C. was most suited for use.

Performance Test

The collagen sponge specimens obtained in Example 2 (10 cm in width, 20 cm in length, 2 mm in thickness) were wetted with physiological saline. The sponge specimens were pulled by "Autograph S-100 WZ" (trade name for product of Shimadzu Seisakusho K.K., Japan) at a rate of 5 mm/min until the sponge broke, whereby there were determined the strength and elongation at the breaking point and Young's modulus as measured from the inclination in the graph.

Table 2 below shows the results. Sponge specimens obtained by washing with distilled water after crosslinking reaction with glutaraldehyde in Example 1 were provided as sponges in Comparison Example 3 for comparative purpose. Table 2 also indicates the results of Comparison Example 3.

TABLE 2

|  | Example 2 | Comp. Example 3 |
| --- | --- | --- |
| Strength ($\times 10^5$ dyne/cm$^2$) | 1.4 ± 0.23 | 1.0 ± 0.32 |
| Young's modulus ($\times 10^5$ dyne/cm$^2$) | 4.5 ± 1.0 | 6.9 ± 2.4 |
| Elongation (%) | 50 ± 7.5 | 41 ± 12 |

Storability Test

The collagen sponge specimens obtained in Examples 1 and 2 were sterilized with an ethylene oxide gas and placed into a bag of aluminum. The hermetically closed bag was stored in an incubator under accelerated test conditions: a temperature of 50° C. and a humidity of 80%.

For comparative purpose, a sponge specimen was prepared by crosslinking reaction and washing in the same manner as in Example 1, immersed in a 70% aqueous solution of ethanol, and stored in a wet condition in a constant-temperature water bath under an accelerated test condition of 50° C.

The test results are shown below. Sponge specimens obtained Examples 1 and 2: the sponges showed no change as in color even in 3 months. Sponge specimen for comparison: The sponge exhibited pronouncedly yellow discoloration in a week.

We claim:

1. A process for preparing a crack-free, dried collagen sponge having a shrinkage factor of up to 14%, comprising the steps of impregnating a crosslinked collagen sponge with an aqueous solution of a hydrophilic organic solvent selected from the group consisting of aliphatic lower alcohols and aliphatic lower ketones, freezing the sponge and the aqueous solution therein at a temperature of −80° C. or lower, and vacuum-drying the sponge, the aqueous solution thereby being removed.

2. A process according to claim 1 wherein the hydrophilic organic solvent is a lower aliphatic alcohol.

3. A process according to claim 2 wherein the lower aliphatic alcohol is ethanol.

4. A process according to claim 1 wherein the crosslinked sponge is impregnated with the aqueous solution of hydrophilic organic solvent so that the solution accounts for at least 90% by volume of the sponge.

5. A process according to claim 1 wherein the freezing step is conducted at a temperature of −80° to about −135° C.

* * * * *